United States Patent [19]

Betancourt

[11] 4,180,076

[45] Dec. 25, 1979

[54] NASOGASTRIC CATHETERS

[76] Inventor: Victor M. Betancourt, Pedro Laplace No. 30 Apt. 3 Colonia Nueva Anzures, Mexico 5 D. F., Mexico

[21] Appl. No.: 869,206

[22] Filed: Jan. 13, 1978

[30] Foreign Application Priority Data

May 6, 1977 [MX] Mexico .................................. 169032

[51] Int. Cl.² ........................................... A61M 25/00
[52] U.S. Cl. .................................................. 128/349 B
[58] Field of Search ............... 128/348, 349 R, 349 B, 128/349, 350, 351, 276, 278

[56] References Cited

U.S. PATENT DOCUMENTS

| | | | |
|---|---|---|---|
| 3,411,506 | 11/1968 | Velasco | 128/349 B |
| 3,889,688 | 7/1975 | Eamkaow | 128/351 |
| 3,908,664 | 9/1975 | Losef | 128/278 X |
| 4,019,515 | 4/1977 | Kornblum et al. | 128/349 BX |
| 4,057,065 | 11/1977 | Thow | 128/348 |
| 4,100,246 | 7/1978 | Frisch | 128/349 BX |

*Primary Examiner*—E. H. Eickholt
*Attorney, Agent, or Firm*—Ladas, Parry, Von Gehr, Goldsmith & Deschamps

[57] ABSTRACT

A nasogastric catheter comprises a tube of relatively flexible material defining a main duct extending from one end of the tube to the other end thereof, and first and second inflatable vessels which are mounted at the exterior of the tube and through which the tube extends. The vessels are situated along the tube approximately three-quarters of the way along the tube from the one end to the other end and are spaced from one another along the tube. First and second subsidiary conduits extend within the tube from the one end and communicate with the first and second vessels respectively but are isolated from said main duct. The tube is formed with at least one lateral perforation between the first and second vessels and a plurality of lateral perforations after the second vessel, the lateral perforations establishing communication between the main duct and the exterior of the tube.

6 Claims, 14 Drawing Figures

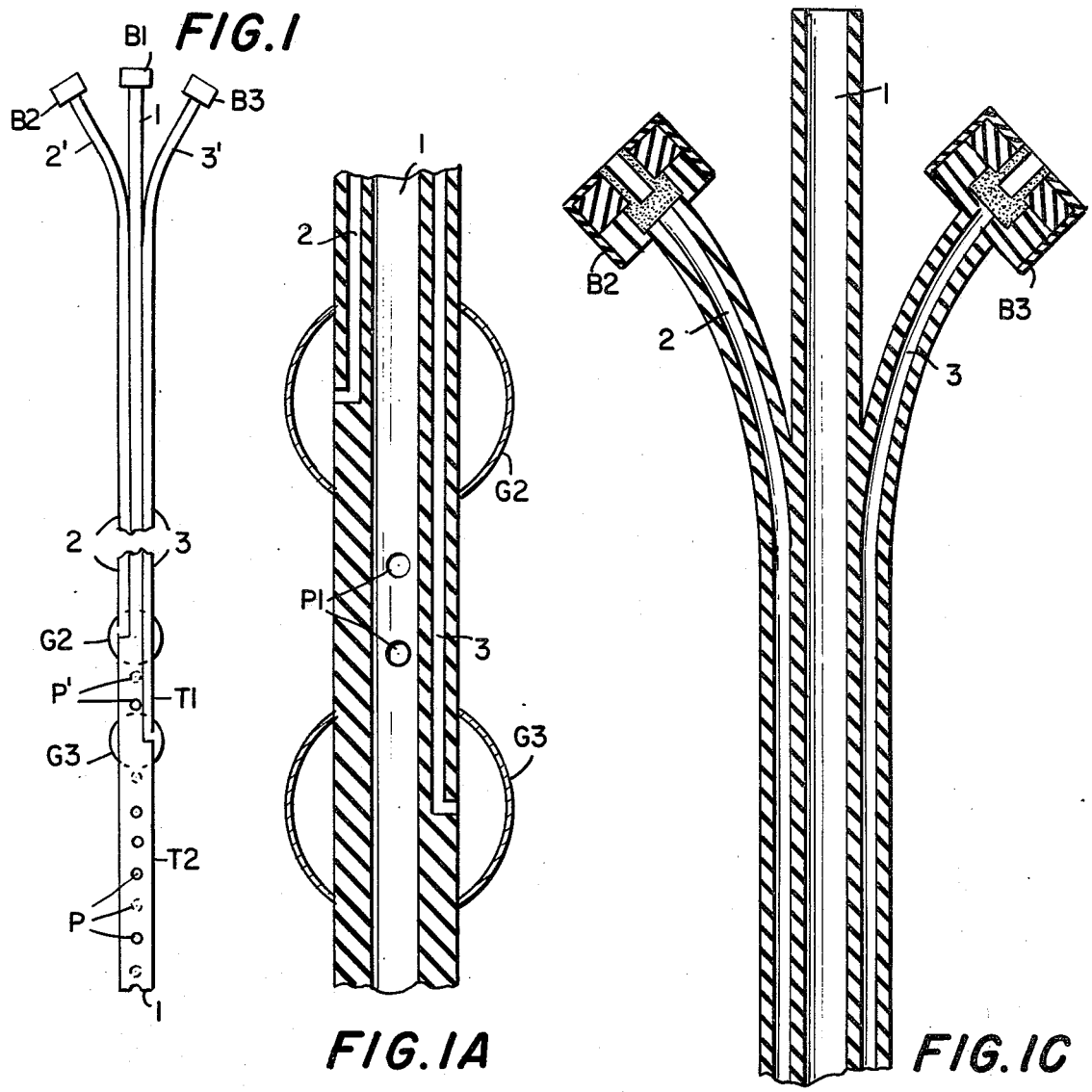
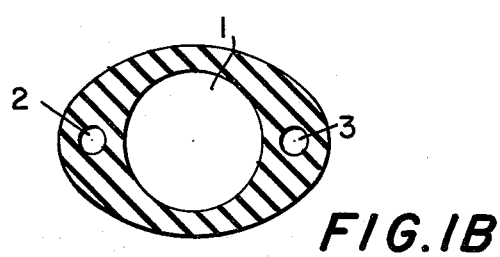

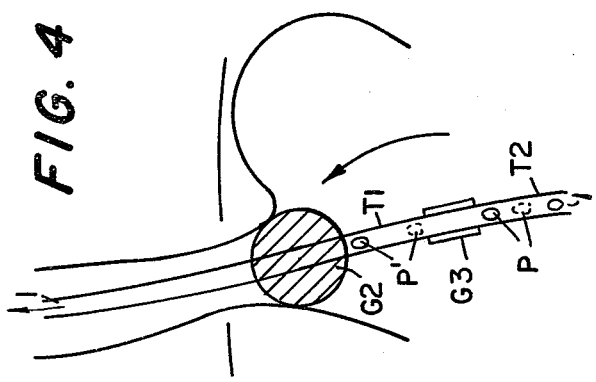
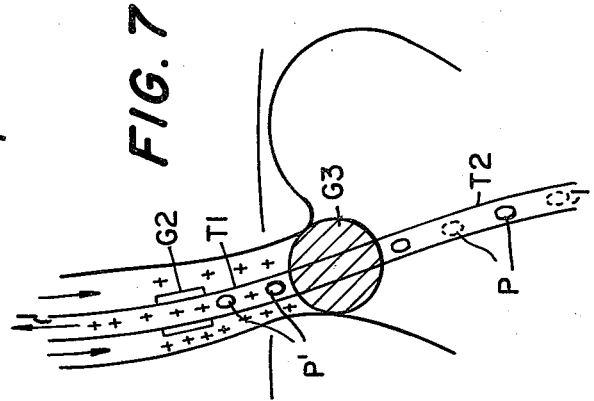
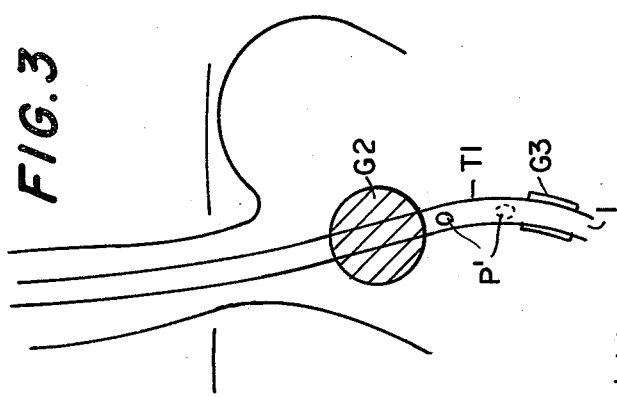
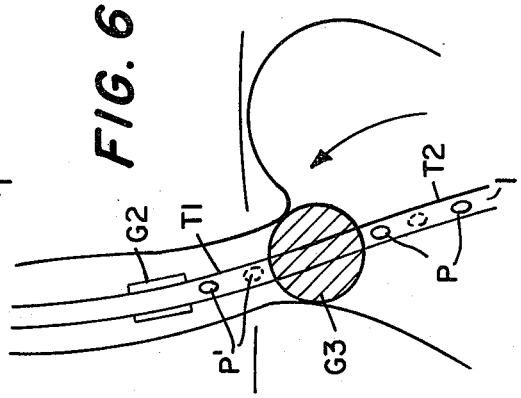
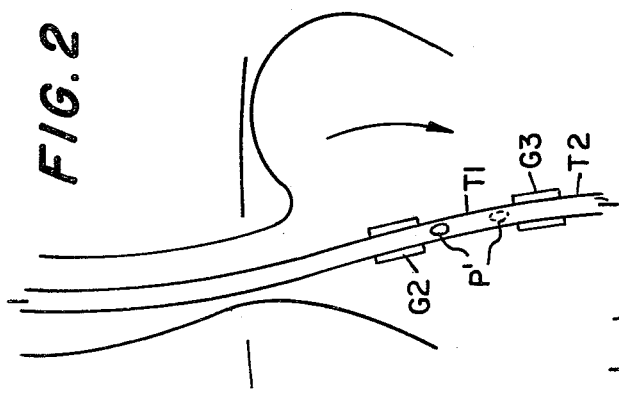
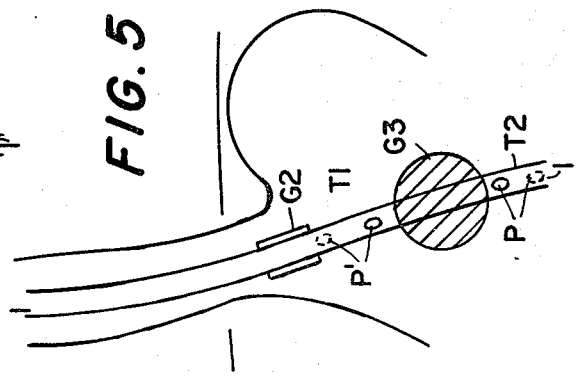

NASOGASTRIC CATHETERS

This invention relates to nasogastric catheters.

It is known to introduce a nasogastric catheter into a patient's stomach cavity by way of his esophagus for the purpose of withdrawing the contents of the stomach by suction in order to control irrepressible vomiting, and for the purpose of feeding a patient who cannot be fed through the mouth.

Nasogastric catheters used at present, such as the Levin catheter, comprise a relatively flexible tube that is simply introduced until it reaches the stomach cavity in order to supply liquid food to a patient who cannot be fed through the mouth.

Catheters of this type have the disadvantage that the patient, either consciously or unconsciously, makes peristaltic contractions or movements of the stomach and the esophagus that may cause the stomach contents to pass up the esophagus and enter the trachea, thereby flowing to the lungs of the patient, which is the reason why the condition of the patient frequently worsens due to complications with penumonia produced by the effusion of food in the respiratory system, death often being the consequence of such conditions.

Mexican patent application No. 162736 describes a nasogastric catheter consisting of a main tube having a single subsidiary conduit integral with the wall of the tube, which conduit has a spout of rigid material adapted for the introduction of a syringe in order to inject air or any fluid to inflate an elongated bag, or to inflate simultaneously two contiguous spherical bags, situated about three-quarters of the way along the catheter.

The nasogastric catheter described in Mexican patent application No. 162736 is suitable only for feeding the patient, eliminating the problems of conventional catheters inasmuch as they prevent the passage of food back up the esophagus to the trachea, since the elongated bag or the two adjacent spherical bags that are interconnected keep the food from passing from the stomach back to the mouth cavity whereby the effusion to the respiratory system is prevented despite the amplitude of the peristaltic wave of the esophagus.

However, this catheter does not remove the discomfort suffered by the patient and the danger of asphyxia attendant upon irrepressible vomiting. Also, the natural secretions of the esophagus accumulate in the esophagus above the inflated bag or bags.

According to the present invention there is provided a nasogastric catheter comprising a tube of relatively flexible material defining a main duct extending from one end of the tube to the other end thereof, first and second inflatable vessels which are mounted at the exterior of said tube and through which said tube extends, said vessels being situated along said tube approximately three-quarters of the way along the tube from said one end to said other end thereof and being spaced from one another along said tube, and first and second subsidiary conduits extending within the tube from said one end and communicating with the first and second vessels respectively but being isolated from said main duct, said tube being formed with at least one lateral perforation between the first and second vessels and a plurality of lateral perforations after the second vessel, the lateral perforations establishing communication between said main duct and the exterior of the tube.

The main duct and the subsidiary conduits may terminate at said one end of the catheter in respective tubular sections, which may be provided with spouts or valves for attaching syringes, feeding devices, etc. in order to supply liquid medicaments or food to the patient and to inflate the two vessels.

The tubular sections of the subsidiary conduits, where they are separated from the main tube, may be different levels from the tubular section of the main tube, or they may be given different colors, or their spouts may be of different colors in order to identify from the outside the conduit to which each tubular section pertains and use it accordingly either for feeding, or for inflating the first and second vessels at the lower end of the catheter, as needed.

The inflatable vessels can be independently inflated, and may have equal or different volumes. The purpose of the vessels is to seal the entrance of the stomach cavity and to prevent the catheter from adhering to the walls of the esophagus or of the stomach cavity and having its perforation(s) obstructed by such contact.

When the objective is the suction of the stomach contents, the first vessel is inflated to its maximum capacity and the catheter is slightly drawn upwards until it touches and seals the entrance of the stomach cavity, and subsequently the second vessel is inflated to the maximum capacity to prevent the catheter from adhering to the walls of the stomach cavity and permit the suction of the stomach contents through the lateral perforation(s) of the main tube.

When a patient is being fed and the entrance of the stomach cavity is sealed by the second vessel that has been inflated to its maximum capacity, the latter will prevent the stomach contents from passing to the esophagus and thus from flowing to the lungs. Under these conditions, if the first vessel is inflated to a lesser degree than the second, the result is that the walls of the esophagus will not adhere to the perforation(s) between the two vessels whereby it becomes possible to extract the buccopharngeal secretions that in these conditions accumulate within the esophagus. After a predetermined period of time the feeding is suspended and the suction is effected through the main tube to extract the secretions accumulated in the pharnx through the perforation(s) between the two vessels, the feeding being resumed when it is deemed necessary. For a better understanding of the invention, and to show how the same may be carried into effect, reference will now be made, by way of example, to the accompanying drawings in which:

FIG. 1 shows a lateral longitudinal view of a nasogastric catheter;

FIGS. 1A, 1B, and 1C illustrate details of the catheter;

FIGS. 2, 3 and 4 illustrate use of the nasogastric catheter for the purpose of extracting a patient's stomach contents;

FIGS. 5, 6, 7 and 8 illustrate use of the catheter for controlling irrepressible vomiting, either while the patient is being fed or during extraction of the stomach contents.

Figure 8:
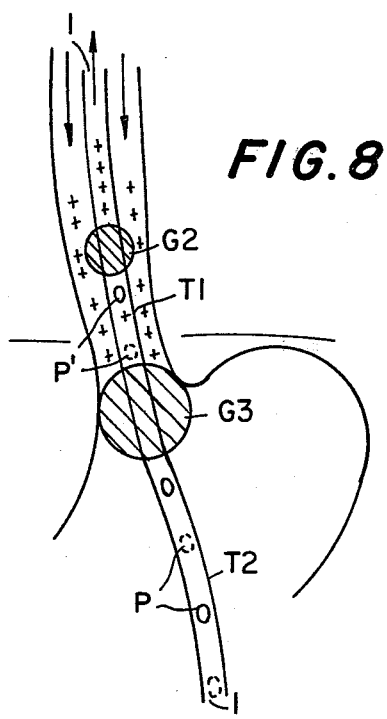
Figure 9:
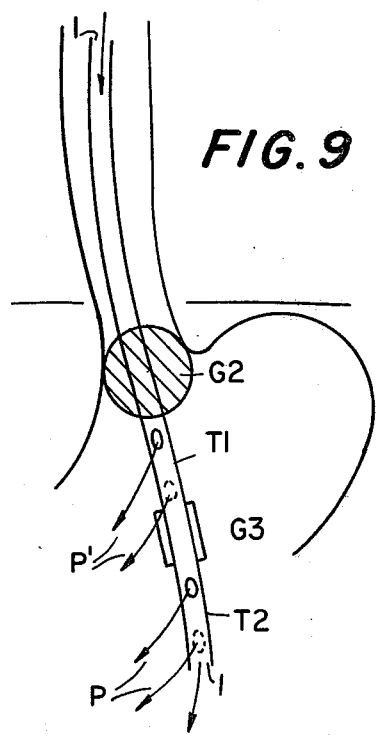
FIGS. 9, 10 and 11 illustrate use of the catheter for feeding a patient who cannot be fed through the mouth.
Figure 10:
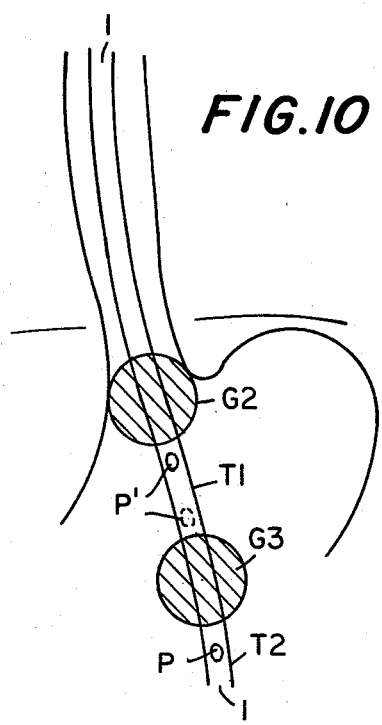
Figure 11:
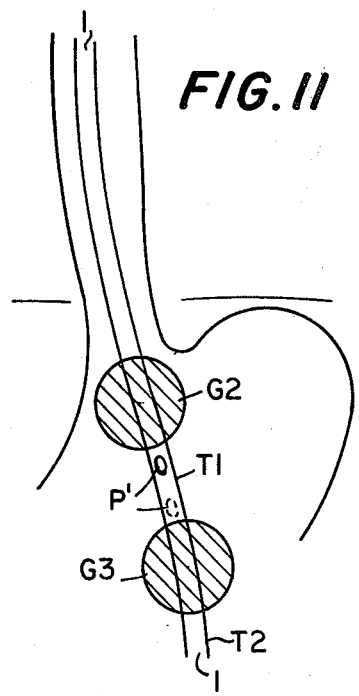

The illustrated nasogastric catheter comprises a main tube 1 of relatively flexible material, i.e. material which is flexible but is nevertheless strong enough to enable the catheter to be introduced via the nasal conduit without being easily flexed. For example, the material may be rubber. The main tube 1 is open at its two ends and extends through two inflatable globes G2 and G3 which are positioned near the lower end of the catheter, approximately three-quarters of the way along the catheter. The main tube 1 has a zone $T_1$ between the globes G2 and G3, and a zone $T_2$ between the globe G3 and the lower end of the tube, the globe G2 being slightly above the globe G3. The wall of the tube 1 is formed with lateral perforations P' and P in the zones $T_1$ and $T_2$. First and second subsidiary conduits 2 and 3 extend within the wall of the tube 1 from the upper end of the tube 1 and open into the globes G2 and G3 respectively. The conduits 2 and 3 are independent of each other and integral with the external surrounding wall of the main tube 1, the upper ends of the conduits 2 and 3 being branched off from the main tube and having tubular sections 2' and 3' respectively. The conduits 2 and 3 enable the globes G2 and G3 to be inflated independently of each other.

The main tube 1 and the tubular section 2' and 3' of the conduits 2 and 3 are provided with valves or spouts B1, B2 and B3 for the attachment of suction syringes or special devices for supplying food or medicines through the main tube and for inflating the globes G2 and G3.

1. - SUCTION OF THE GASTRIC CONTENT PROCEDURE (Adults).
   a.- After applying local anesthesia to the nasal fossa and lubricating the catheter, the latter is introduced in the nasal fossa, up to the beginning of the tubular section 2' (FIG. 1). Thus, the catheter is introduced a distance of 108 cms. (42.5 inches) and approximately 58 cms (23.5 inches) of the catheter will be disposed in the gastric cavity (FIG. 2).
   b.- Suction is applied to the conduit 3 in order to be sure the catheter is inside of the gastric cavity.
   c.- The globe G2 is inflted with 15 c.c. of water (FIG. 3) supplied through the conduit 2.
   d.- The catheter is withdrawn with care, until it stops, (FIG. 4). In this position the globe G2 blocks the esophagus where it opens into the stomach.
   e.- The catheter is secured to the cutaneous tegument with Micropor, which will retain the globe G2 in its position blocking the esophagus.
   f.- Suction is applied to the conduit 3 for the necessary time.

2. - INCOERCIBLE VOMIT PROCEDURE (Adults).
   a.- Carry out steps a, b, c, d and e of the procedure for suction of the gastric content.
   b.- The conduit 3 is connected to an empty food supply equipment.

3. - FEEDING PROCEDURE (Adults).
   (A) If the catheter is in phase of SUCTION (FIG. 4), i.e. in the course of step f of the procedure for suction of the gastric content.
      (i) Without pathology in upper or lower respiratory tract (without abnormal secretions).
         a.- The suction is removed, and the conduit 3 is connected to a food supply equipment.
         b.- In the same position the passing of foods is carried out through conduit 3 (FIG. 4). It takes 3 or 4 minutes to pass the food.
         c.- When the food in the food supply equipment is finished the catheter must remain in the same position, until the next feeding.
         d.- Once every 12 hours, is necessary to do the following operation before the administration of food:
            - The globe G2 is deflated by extracting the 15 c.c. of water and the globe G3 is inflated with 15 c.c. of water (FIG. 5).
            - The catheter is withdrawn with care, until it stops (FIG. 6). In this position the globe G3 blocks the esophagus where it opens into the stomach.
            - The catheter is secured to the cutaneous tegument with Micropor, which will secure the globe G3 in its position blocking the esophagus.
            - Suction ($-10$ at $-20$) is applied to the conduit 3 and serves to extract by way of the orifices P' the secretions (saliva, etc.) that have accumulated in the esophagus (the marks + epresent the secretions) (FIG. 7). The removal of secretions is facilitated if the globe G2 is partially inflated with 3 c.c. of water (FIG. 8) so that it is approximately 15 mm in diameter (the esophagus being from 25 to 28 mm in diameter), thus avoiding adhesion of the esophagus' walls to the catheter and consequent blocking of the passage of the accumulated secretions into the main tube 1 by way of the orifices P'.
            - When the extraction of secretions is finished, the globe G3 is deflated (by extracting the 15 c.c. of water), just as the globe G2 is deflated if it was partially inflated as described above (by extracting the 3 c.c. of water), and the catheter is inserted into the gastric cavity by a further 5 inches (FIG. 2).
            - The globe G2 is inflated with 15 c.c. of water (FIG. 3).
            - The catheter is withdrawn with care, until it stops (FIG. 4).
            - The catheter is secured to the cutaneous tegument, whereby the globe G2 is retained in this position.
         e.- Repeat steps b and c.
      (ii) With pathology in upper and lower respiratory tract (with abundant secretions).
         a.- Carry out steps (i) a and (i) b.
         b.- Carry out steps (i) d with every introduction of food into the gastric cavity (this is at the physician's discretion): if between two successive introductions of food the secretions taken out by the suction, are 200 to 300 ml., it is necessary to repeat the suction before the next introduction of food. If the secretions are more than 300 ml. it is advisable to apply suction continually after the introduction of the food until the next introduction of food until the next introduction of food.
            - When it is desired to secure the catheter, it my be secured to the cutaneous tegument.
   (B) CATHETER BEING USED IN TREATMENT OF INCOERCIBLE VOMITING
      (i) Without pathology in upper and lower respiratory tract (without abnormal secretions).
         a. - The empty food supply equipment is removed and the conduit 3 is connected to a food supply equipment.
         b. - Carry out steps b, c, d and e of procedure (A) (i).
      (ii) With abundant secretions.

a. - The empty food supply equipment is removed and the conduit 3 is connected to a food supply equipment.
b. - Carry out steps b and c of procedure (A) (i).
c. - At each administration of food carry out step d of procedure (A) (i).
d. - When the catheter is in the position shown in FIG. 4, the conduit 3 is connected to an empty food supply equipment, and the catheter remains in this position, connected to the empty food supply equipment, until the next feeding.

(C) CATHETER TO BE INTRODUCED.
a.- Carry out steps a, b, c, d and e of the procedure for suction of the gastric content.
b.- Carry out steps b, c, d and e of procedure (A) (i), or alternatively, if desired, carry out the steps of procedure (A) (ii).

NOTE: If the catheter is to be removed, the globes are deflated before removal.

It will be appreciated that the invention is not limited to the particular construction that is described and illustrated, since variations my be made without departing from the scope of the invention as defined in the appended claims.

We claim:

1. A nasogastric catheter comprising a tube of relatively flexible material defining a main duct extending from one end of the tube to the other end thereof, first and second inflatable vessels which are mounted at the exterior of said tube and through which said tube extends, said vessels being situated approximately three-quarters of the way along the tube from said one end to said other end thereof and being spaced from one another along said tube, and first and second subsidiary conduits extending within the tube from said one end and communicating with the first and second vessels respectively but being isolated from said main duct, said tube being formed with at least one lateral perforation between the first and second vessels and a plurality of lateral perforations after the second vessel, the lateral perforations establishing communication between said main duct and the exterior of the tube.

2. A catheter as claimed in claim 1, wherein said main duct and said subsidiary conduits terminate in respective tubular sections at said one end of the tube.

3. A catheter as claimed in claim 2, wherein said tubular sections are provided with spouts or valves for attachment of other apparatus to the catheter.

4. A catheter as claimed in claim 2, wherein the tubular sections of the subsidiary conduits terminate at a different position along the catheter from the tubular section of the main duct.

5. A catheter as claimed in claim 2, wherein the tubular sections of the subsidiary conduits are colored differently from the tubular section of the main duct.

6. A catheter as claimed in claim 3, wherein the spouts or valves of the subsidiary conduits are colored differently from the spout or valve of the main duct.

* * * * *